(12) United States Patent
Kaplan

(10) Patent No.: US 6,331,163 B1
(45) Date of Patent: Dec. 18, 2001

(54) PROTECTIVE COATING FOR BODILY SENSOR

(75) Inventor: Shay Kaplan, Givat Ela (IL)

(73) Assignee: Microsense Cardiovascular Systems (1196) Ltd., Givat Ela (IL)

( * ) Notice: Subject to any disclaimer, the term of this patent is extended or adjusted under 35 U.S.C. 154(b) by 0 days.

(21) Appl. No.: 09/354,631

(22) Filed: Jul. 16, 1999

Related U.S. Application Data

(63) Continuation-in-part of application No. 09/004,420, filed on Jan. 8, 1998.

(51) Int. Cl.[7] .......................................................... A61B 5/02
(52) U.S. Cl. .................. 600/486; 73/54.41; 600/373; 600/377; 600/438
(58) Field of Search .................................. 600/345–347, 600/364–365, 371–381, 438, 486, 437, 504–505, 508, 561, 581; 128/DIG. 21; 73/54.41

(56) References Cited

U.S. PATENT DOCUMENTS

| | | |
|---|---|---|
| 3,460,975 | 8/1969 | Siebleton . |
| 3,958,562 | 5/1976 | Hakim et al. . |
| 4,240,438 | 12/1980 | Updike et al. . |
| 4,274,423 | 6/1981 | Mizuno et al. . |
| 4,468,948 | 9/1984 | Nakayama . |
| 4,485,800 | 12/1984 | Anderson et al. . |
| 4,485,831 | 12/1984 | Anderson . |
| 4,673,584 | 6/1987 | Nygren et al. . |
| 4,732,042 | 3/1988 | Adams . |
| 4,823,800 | 4/1989 | Compos . |
| 4,938,827 | 7/1990 | Leach et al. . |
| 4,948,491 | 8/1990 | Kato et al. . |
| 4,993,265 | 2/1991 | Koen et al. . |
| 5,045,151 | 9/1991 | Edell . |
| 5,053,048 | * 10/1991 | Pinchuk ....................... 128/DIG. 21 |
| 5,059,211 | 10/1991 | Stack et al. . |
| 5,067,491 | 11/1991 | Taylor, II et al. . |
| 5,075,127 | 12/1991 | Yafuso et al. . |
| 5,186,808 | 2/1993 | Yamaguchi et al. . |
| 5,212,988 | 5/1993 | White et al. . |
| 5,286,364 | 2/1994 | Yacynych et al. . |
| 5,287,861 | 2/1994 | Wilk . |
| 5,290,231 | 3/1994 | Marcadis et al. . |
| 5,353,800 | 10/1994 | Pohndorf et al. . |
| 5,383,465 | 1/1995 | Lesny et al. . |
| 5,411,550 | 5/1995 | Herweck et al. . |
| 5,411,551 | 5/1995 | Winston et al. . |

(List continued on next page.)

FOREIGN PATENT DOCUMENTS

| | | |
|---|---|---|
| 0 706 783 | 4/1996 | (EP) . |
| 0 709 067 | 5/1996 | (EP) . |
| 2 333 044 | 7/1999 | (GB) . |
| WO 83/03348 | 10/1983 | (WO) . |
| WO89/06513 | 7/1989 | (WO) . |
| WO 92/21284 | 12/1992 | (WO) . |
| WO 98/29030 | 7/1998 | (WO) . |

Primary Examiner—Cary O'Connor
Assistant Examiner—Ryan Carter
(74) Attorney, Agent, or Firm—Kenyon & Kenyon

(57) ABSTRACT

A device and method for fixation of a sensor in a bodily lumen, in which a sensor support is coupled to a fixation device, which is inserted into a bodily lumen. The fixation device is then secured within the bodily lumen, for example, by expansion or by suturing to the bodily lumen. The fixation device may be a stent or a dedicated anchoring ring having a sensor support coupled thereto. The fixation device may be inserted during an intervention procedure or during a special insertion procedure. The sensor may be remotely interrogated exterior to the bodily lumen periodically or continuously. Furthermore, the sensor may be provided with permanent and/or temporary protective coatings to protect it from damage.

18 Claims, 12 Drawing Sheets

U.S. PATENT DOCUMENTS

| | | |
|---|---|---|
| 5,433,216 | 7/1995 | Sugrue et al. . |
| 5,454,373 | 10/1995 | Koger et al. . |
| 5,456,251 | 10/1995 | Fiddian-Green . |
| 5,477,855 | 12/1995 | Schindler et al. . |
| 5,488,957 | 2/1996 | Frey et al. . |
| 5,511,547 | 4/1996 | Markle et al. . |
| 5,516,413 | 5/1996 | Foster et al. . |
| 5,531,878 | 7/1996 | Vadgama et al. . |
| 5,540,828 | 7/1996 | Yacynych et al. . |
| 5,550,790 | 8/1996 | Velamoor et al. . |
| 5,561,522 | 10/1996 | Rapoport et al. . |
| 5,564,434 * | 10/1996 | Halperin et al. ................. 600/561 X |
| 5,580,699 | 12/1996 | Layman et al. . |
| 5,589,396 | 12/1996 | Frye et al. . |
| 5,600,071 | 2/1997 | Sooriakumar et al. . |
| 5,606,974 | 3/1997 | Castellano et al. . |
| 5,616,338 | 4/1997 | Fox, Jr. et al. . |
| 5,619,997 | 4/1997 | Kaplan . |
| 5,623,275 | 4/1997 | Miller . |
| 5,624,537 | 4/1997 | Turner et al. . |
| 5,629,538 | 5/1997 | Lipphardt et al. . |
| 5,630,844 | 5/1997 | Dogan et al. . |
| 5,656,830 | 8/1997 | Zechman . |
| 5,676,820 | 10/1997 | Wang et al. . |
| 5,682,899 * | 11/1997 | Nashef et al. ................... 600/549 X |
| 5,695,155 | 12/1997 | Macdonald et al. . |
| 5,711,861 | 1/1998 | Ward et al. . |
| 5,711,868 | 1/1998 | Maley et al. . |
| 5,711,915 | 1/1998 | Siegmund et al. . |
| 5,744,902 | 4/1998 | Vig . |
| 5,759,364 | 6/1998 | Charlton et al. . |
| 5,766,956 | 6/1998 | Groger et al. . |
| 5,767,687 | 6/1998 | Geist . |
| 5,776,324 | 7/1998 | Usala . |
| 5,786,439 | 7/1998 | Van Antwerp et al. . |
| 5,814,526 | 9/1998 | Tseng . |
| 5,823,957 | 10/1998 | Faupel et al. . |
| 5,843,076 | 12/1998 | Webster, Jr. et al. . |
| 5,867,886 | 2/1999 | Ratell et al. . |
| 5,869,244 | 2/1999 | Martin et al. . |

\* cited by examiner

PROTECTIVE COATING FOR BODILY SENSOR

RELATED APPLICATION INFORMATION

This application is a continuation-in-part of U.S. patent application No. 09/004,420 filed Jan. 8, 1998.

FIELD OF THE INVENTION

The present invention relates generally to a method and device for fixation of a sensor in a bodily lumen and for protection of the sensor during insertion into a bodily lumen.

BACKGROUND OF THE INVENTION

Sensors for the monitoring and/or recordation of various human physical, chemical and/or physiological parameters are known in the art. U.S. Pat. No. 4,485,813 describes a sensor that may be permanently implanted in a specific location within the human body in an implantable medical device such as a pacemaker. This sensor is used to monitor certain physical and/or physiological parameters of the subject in which it has been implanted. This sensor can be maintained in the subject for extended periods of time to continuously monitor information about the subject.

A severe limitation to the sensor described in U.S. Pat. No. 4,485,813 is the limited number of possible locations in which it can be implanted due to the requirement that the sensor be located in a medical device such as a pacemaker and the difficulty of fixation independently. This limitation on the location and fixation of the sensor limits the usefulness of the sensor for inter-lumen applications.

Sensors used to monitor parameters within lumens include sensors made of very thin membranes that are highly sensitive to mechanical pressure. As a result there is a great risk of the sensor being damaged during insertion, deployment and/or positioning. Damage to the sensor could result in poor performance or non-operability of the sensor. For example, should the membrane of a sensor break during insertion, the sensor would be rendered inoperable. Due to the risks associated with the procedures for the insertion of sensors, there would be great costs and risks involved should a sensor be damaged or destroyed during insertion. Thus, there is also a need for a device and method of protecting sensors during insertion and fixation.

For such sensors, including those machined from silicon, another concern is the erosion that the pressure-sensitive membrane undergoes when it is implanted in a patient and exposed for a prolonged period of time to bodily fluids and other naturally occurring agents inside the patient. Contrary to the prevalent view, it was discovered that a sensor machined from silicon does not exhibit a satisfactory degree of bio-compatibility with the naturally occurring bodily fluids and agents it encounters when implanted inside a patient. After a certain amount of time, these fluids and agents slowly begin dissolving the sensor, degrading the accuracy of the data produced by the sensor, and indeed, after a period of a few months, dissolving the thin membrane and other parts of the sensor completely. What is therefore needed is a bio-compatible protective coating for the sensor that resists the corrosive effect of the human body's naturally occurring fluids. By minimizing the erosion of the sensor membrane, such a protective coating would not only extend the useful life of the sensor, the coating would also maintain the accuracy of the data produced by the sensor while it is implanted inside the patient.

SUMMARY OF THE PRESENT INVENTION

It is, therefore, an object of the present invention to provide a method and device for fixation of a sensor in a bodily lumen. Through the use of such a method and device, remotely interrogated sensors may be fixed within bodily lumens. Such sensors may be used to record and/or monitor parameters such as, for example, physiological parameters, e.g., pressure and velocity of flow, and biochemical parameters, e.g., level of gases and biochemical substances in the fluid contained in the lumen.

The monitoring of conditions in lumens today dictates some level of intervention and/or intrusion and the frequency of such monitoring is limited by the relative risk of the required intervention. The present invention, therefore, provides a sensor device which may be implanted, either temporarily or permanently, in a lumen and interrogated from an exterior position, for example, the surface of the body, at any time without any physical intrusion.

The present invention provides a method and device for the fixation of such sensors in specific desired locations and/or preferred positions in the lumen. Such fixation of the sensors may be achieved at the time of any required surgical intervention or independently by catheterization. Furthermore, the sensor may be connected to the repair device, e.g., the stitches of a bypass, an aneurismal repair device, a stent, etc., or mounted on its own dedicated fixation device.

A sensor may be fixed inside a lumen by any number of means, including directly attaching the sensor in place, for example, by including holes in the sensor, e.g., around its periphery, and attaching the sensor to the stitches of a bypass during surgery, or through the use of a surgical adhesive. A sensor may also be positioned inside a lumen using a carrier or support (of any shape and size) which may be part of, or coupled to a repair device, e.g., a stent or aneurismal correction device which holds the sensor in place adjacent to or near the repair device. Additionally, a sensor may be positioned inside a lumen using a dedicated device, e.g., an anchoring ring, which is held within a lumen and fixed in place, for example, by expansion with a catheter balloon. A dedicated device may be used, for example, when fixation is necessary but no corrective device is employed at the desired location. The anchoring ring does not necessarily have to be circular in shape, but may instead be oval or any other shape best suited for the location where placed. Additionally, the anchoring ring may have a separate carrier or support to hold the sensor. The carrier or support may be any shape or size, including, for example, circular, square, rectangular, diamond shaped, linear with or without a bent or curved end, etc, and it may be constructed as only a border or as a solid piece of material. As discussed below, the anchoring ring may be expandable by a balloon catheter, or some other method, such as self expansion.

Multiple sensors may be attached to a carrier or carriers, for example, two sensors with one placed on each side of a stent, or two sensors attached at both connections of a bypass section, e.g., one sensor at the entrance to an aneurismal sleeve and one at the outside of the sleeve to monitor for a possible leak around the sleeve. Additionally, a sensor may have multiple repair devices or dedicated devices supporting it within a lumen, either with or without a carrier, for example, a sensor supported between two anchoring rings.

A sensor may be supported by or connected to a carrier, for example, by providing a groove-like depression(s) or notch-like depression(s) in the sensor into which a portion(s) of the carrier may be inserted, or the sensor may be configured such that a portion(s) of the sensor, for example, a lip-like extension(s) or protrusion(s), may extend beyond the dimensions of the carrier to be supported thereby. Additionally, the sensor may be attached to the carrier, for example, by welding and/or glueing or any combinations of the above.

After a sensor is fixed within a lumen, for example, during an intervention procedure such as aneurismal device implantation, PTCA, coronary bypass surgery, etc., it may thereafter be monitored periodically to track any of a variety of parameters or to assess the effectiveness of the procedure that was performed. For example, the sensor may be monitored periodically to assess the long term progress or deterioration of the corrective effect, and the progress of relevant symptoms of a disease.

Multiple sensors may be implanted and may be monitored individually or simultaneously to derive gradients along a lumen and across a repair device or section. Such sensors may be fixed in any number of positions within a lumen, for example, on both sides of a lesion treated by PTCA with or without a stent, on both sides of a bypass section, and before, after and around an aneurismal repair device, etc.

The fixation device may be constructed by first creating a flat version of the desired pattern for the fixation device, for example, from a piece of thin stainless steel sheet metal or some other material, e.g., any metal, non-metallic or bioabsorbable material. The flat pattern can be produced through any suitable technique, such as etching the design into the sheet metal, by cutting with a very fine laser, or by any other technique.

Once the material has been cut, it is deformed so as to cause its edges to meet. To create a fixation device from a flat, metal pattern, the flat metal is rolled until the edges meet. The portion which holds the sensor may be located along the circumference of the fixation device, may extend perpendicular to the cross-section of the ring formed or may extend in some other manner from the ring formed by the fixation device. The locations where edges meet are joined together, such as by spot welding. Afterwards, the fixation device is polished, either mechanically or electrochemically. As shown in the figures, the fixation device may also be formed, for example, by etching from tubing, building from wires (e.g., as a cylinder), etc.

The present invention is also directed to a sensor having a protective layer applied to a surface thereof. The protective layer prevents degradation, for example, of the sensor membrane, by agents present in the body fluid (e.g., blood) and/or in the living tissue of the body. Such degradation could impair the operation of the sensor or render it inoperative. According to the present invention, the protective layer includes an inert, bio-compatible material applied to the sensor, wherein the layer is preferably thin, uniform and flexible enough so as not to interfere with the sensitivity of the sensor. Examples of suitable materials include silicone rubber, Teflon, or a polyxylylene polymer material such as, for example, Parylene C. In the case of silicone rubber and Teflon serving as the protective layer, the protective layer may be applied to the sensor by a spin-coating operation. In the case of the polyxylylene polymer material serving as the protective layer, the protective layer may be deposited onto the sensor by a vapor deposition process.

The present invention also provides for a device and method for additional or alternative temporary protection of sensors during insertion. In order to preserve sensors during insertion and remove the risk of damage to or destruction of sensors during an insertion or positioning procedure, sensors may be coated with an additional or alternative temporary protective layer (e.g., biocompatible), which is soluble in an aqueous solution, and which disappears immediately or soon after deployment of the sensor in the body. The material used for, thickness of, and hardness of the coating may vary, for example, depending on the location of the sensor, the type of sensor, protection level sought, and rate of dissolution desired.

BRIEF DESCRIPTION OF THE DRAWINGS

The present invention will be understood and appreciated more fully from the following detailed description taken in conjunction with the drawings in which.

DETAILED DESCRIPTION

Figure 1A:
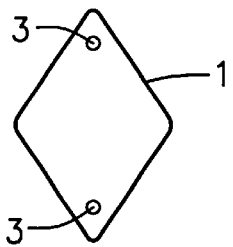
FIG. 1A is a drawing of a first fixation device for a sensor according to a preferred embodiment of the present invention.
Figure 1B:
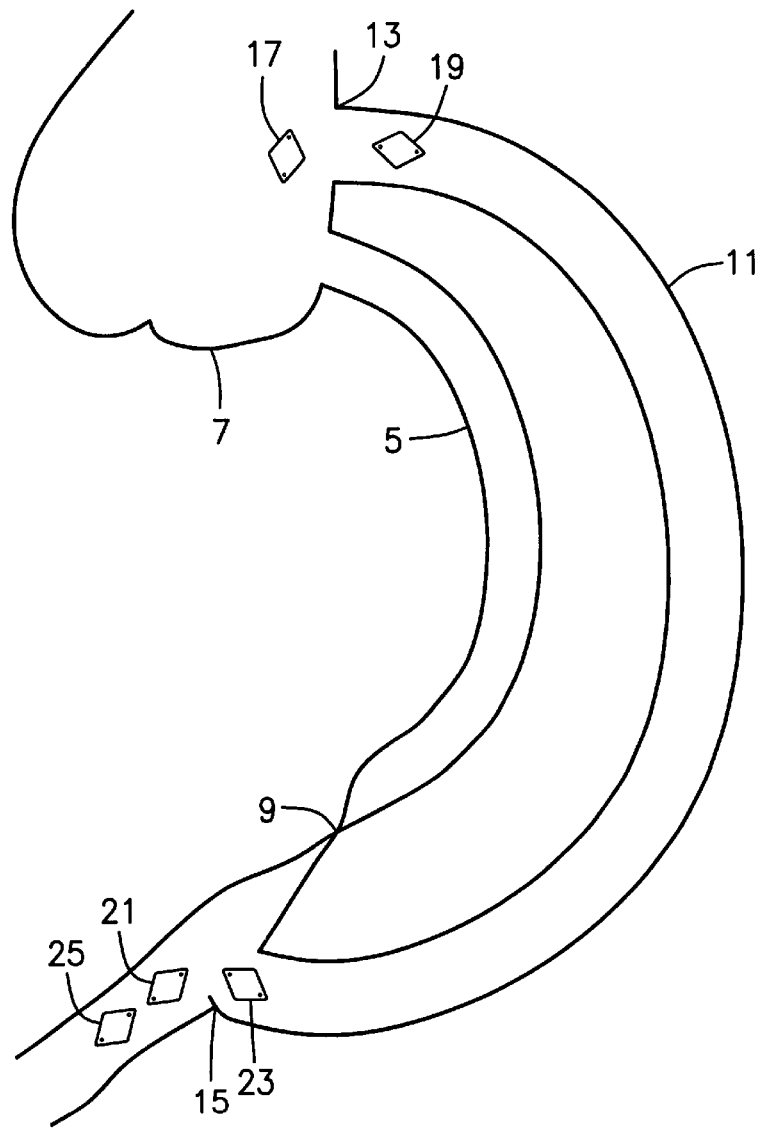
FIG. 1B is an illustration of a method for fixation of the sensor of FIG. 1A within a lumen according to a preferred embodiment of the present invention.

Reference is now made to FIGS. 1A and 1B, which illustrate a first fixation device for a sensor and a first method for fixation of a sensor within a lumen, respectively, according to a preferred embodiment of the present invention.

In FIG. 1A, there is shown a sensor 1 having two holes 3 in its periphery for attachment to sutures within a lumen. In FIG. 1B, there is shown a coronary artery 5 starting at the Aorta 7 and having an occlusion 9. A bypass 11 is connected between the Aorta at point 13 and at point 15 beyond the occlusion 9. Sensor 1 is placed either at the proximal ostium 17 or at the proximal part of the bypass 19. Alternatively, sensor 1 may be placed at the distal ostium 21, at the distal part before the distal ostium 23, or at the distal part after the distal ostium 25. Any number of sensors may be used, and they may be placed in any combination of the above positions or any other position desired. The sensor 1 is fixed in place using the two holes 3 for attachment to the sutures. Alternatively, the sensor 1 may be fixed in place using surgical adhesive or a surgical staple(s).

Figure 2A:
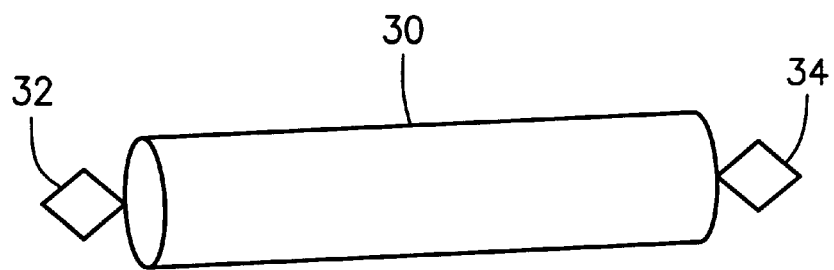
FIGS. 2A and 2B show illustrations of a second fixation device for a sensor before expansion and after expansion, respectively, according to a preferred embodiment of the present invention.
Figure 2B:
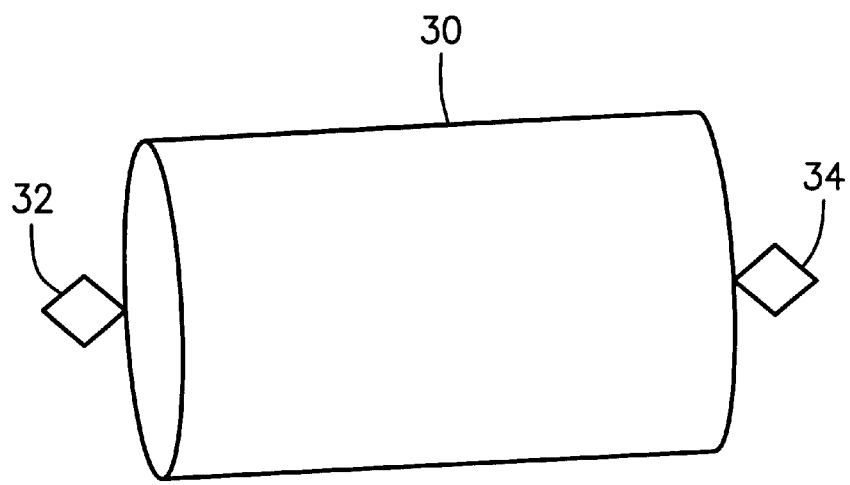

Referring now to FIGS. 2A and 2B, there are shown a second fixation device for a sensor before expansion and after expansion, respectively, according to a preferred embodiment of the present invention.

In FIG. 2A, there is shown a stent 30 in a non-expanded state with a first sensor support 32 and a second sensor support 34. Alternatively, the stent 30 may include only one or more than two sensor supports. For example, a third sensor support may be located opposite the first sensor support 32. In FIG. 2B, the stent 30 from FIG. 2A is shown in its expanded state. Expansion may be accomplished, for example, by balloon catheterization or some other procedure, such as, for example, self expansion. To fix a sensor within a lumen, the stent 30 is positioned as it normally would be during any medical procedure in which a stent is used. Prior to expansion, and either prior to or after insertion of the stent 30 into the lumen, a sensor is placed in, placed on or attached to the first sensor support 32 and/or the second sensor support 34. The stent 30 is then either expanded, or inserted into the lumen and then expanded. The same procedure may be used to fix any number of sensors within a lumen, with the additional step of placing each sensor either in or on, or attaching each sensor to its corresponding sensor support.

Figure 3A:
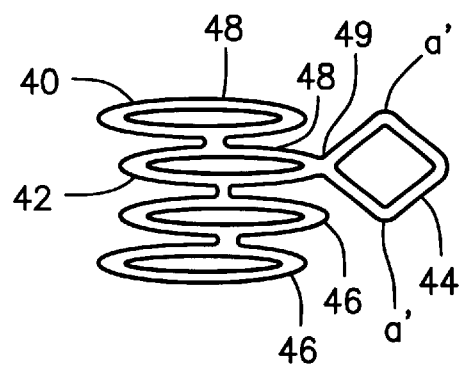
FIGS. 3A and 3B show illustrations of a third fixation device for a sensor before expansion and after expansion, respectively, according to a preferred embodiment of the present invention.
Figure 3B:
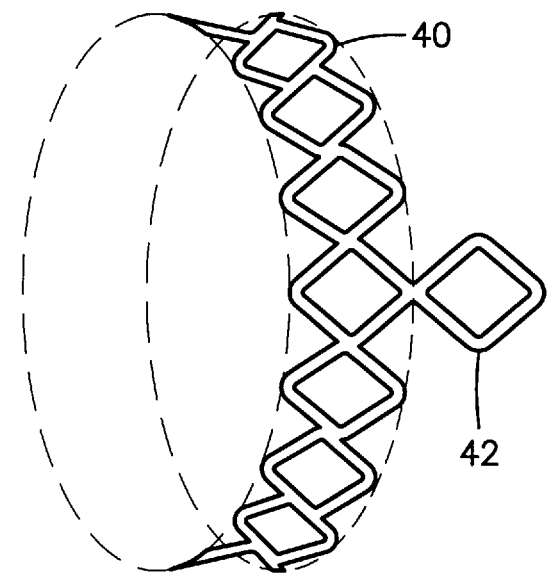

Referring now to FIGS. 3A and 3B, there are shown a third fixation device for a sensor before expansion and after expansion, respectively, according to a preferred embodiment of the present invention.

In FIG. 3A, there is shown a fixation device 40 in the form of an anchoring ring 42, in a non-expanded state coupled to a sensor support 44. The fixation device 40 may be formed of any malleable material which does not revert automatically to its original shape after being expanded. The anchoring ring 42 is made up of a plurality of elliptical sections 46 connected one to the other at the middle of each of their long portions 48 to form a ring. The sensor support 44 is connected to one of the elliptical sections 46 at a short portion 49, and perpendicular to a cross-section of the anchoring ring 42 forming a circular plane. The sensor support 44 is formed in the shape of a diamond, but can be any shape desired. Additionally, there may be multiple sensor supports attached to the anchoring ring 42. Alternatively, the anchoring ring 42 may be made of a single sinusoidal ring, with one or more sensor supports attached to the peaks, since it does not serve any support function for the lumen.

FIG. 3B shows the fixation device 40 of FIG. 3A in an expanded state. To fix a sensor within a lumen, the fixation device 40, in the form of an anchoring ring 42, is positioned within the lumen, for example, during an intervention procedure, and expanded, for example, by balloon catheterization or some other procedure. Prior to expansion, and either prior to or after insertion of the fixation device 40 into the lumen, the sensor is placed in, placed on or attached to the sensor support 44. The fixation device 40 is then either expanded, or inserted into the lumen and then expanded. The same procedure may be used to fix multiple sensors within a lumen, with the additional step of placing each sensor either in or on, or attaching each sensor to a corresponding sensor support.

Figure 4:
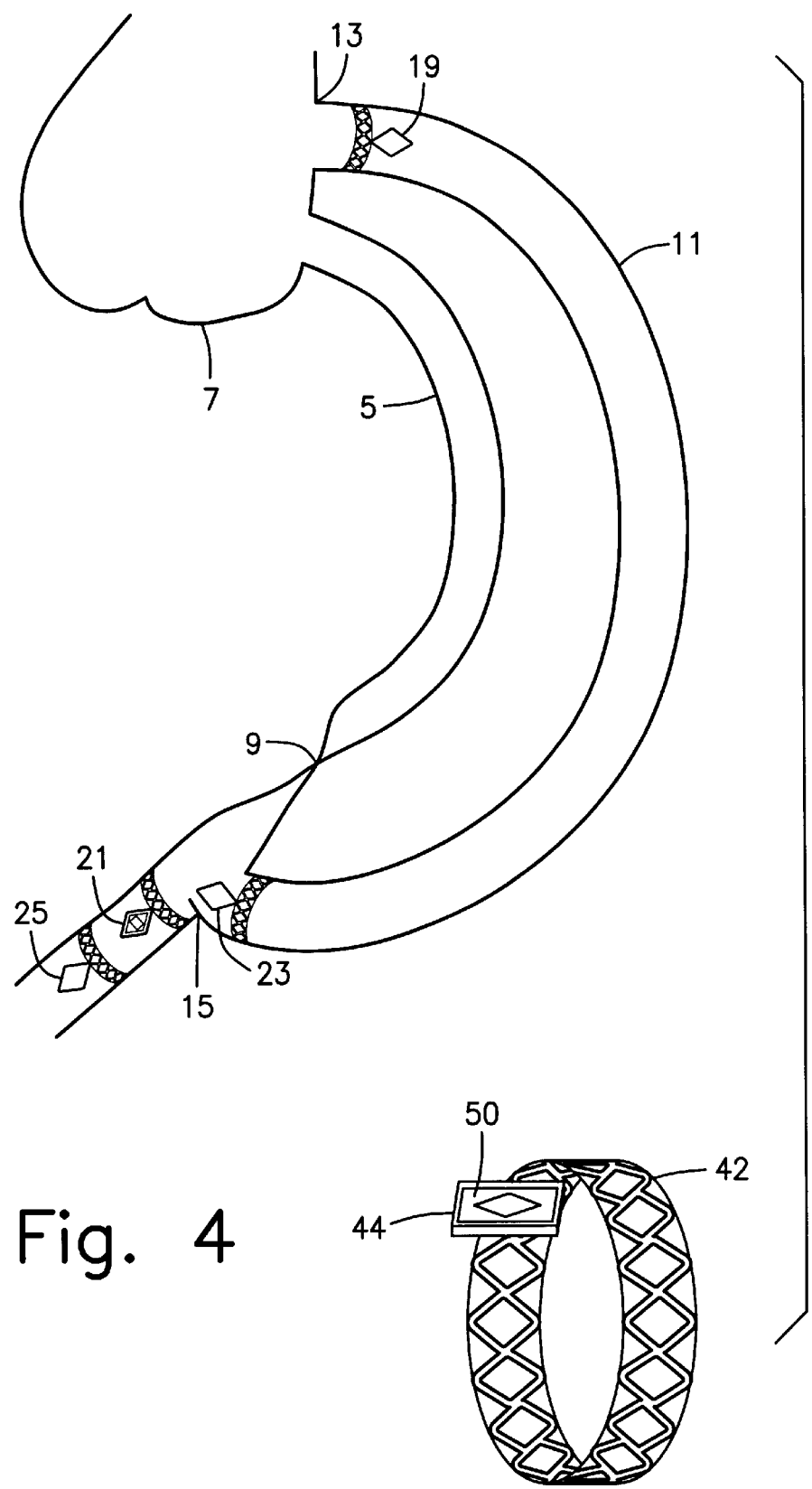
FIG. 4 illustrates a second method for fixation of a sensor within a lumen using the third fixation device shown in FIGS. 3A and 3B, according to a preferred embodiment of the present invention.

Referring now to FIG. 4, which illustrates a second method for fixation of a sensor within a lumen using the third fixation device shown in FIGS. 3A and 3B, according to a preferred embodiment of the present invention. As illustrated in FIG. 1B, a coronary artery 5 starting at the Aorta 7 and having an occlusion 9 is fitted with a bypass 11 which is connected between the Aorta at point 13 and at point 15 beyond the occlusion 9. Sensor 50, which is carried by the sensor support 44 coupled to the anchoring ring 42 of FIGS. 3A and 3B, is placed either at the proximal part of the bypass 19, at the distal ostium 21, at the distal part before the distal ostium 23, or at the distal part after the distal ostium 25. Any number of sensors may be used, and they may be placed in any combination of the above positions or any other position desired in which an anchoring ring can be used. The sensor 50 is fixed in place by expansion using balloon catheterization.

Figure 5:
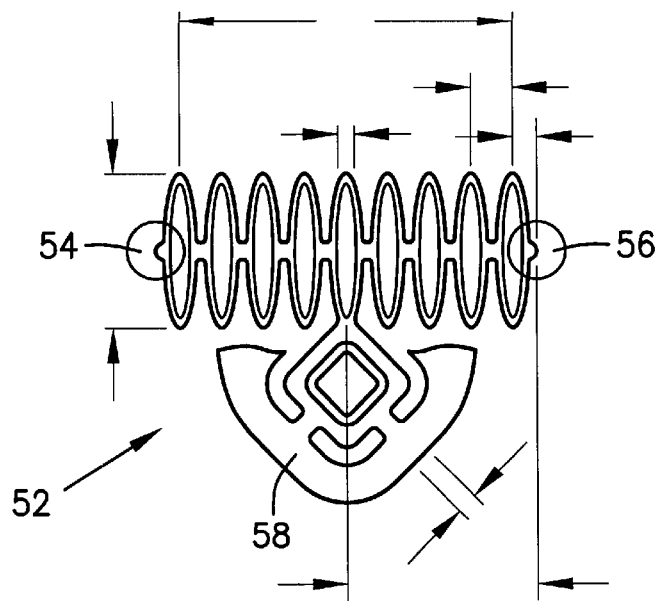
FIG. 5 shows an illustration of a mask for etching of a flat design of the fixation device of FIGS. 3A and 3B, according to a preferred embodiment of the present invention.

Referring now to FIG. 5, there is shown an illustration of a mask for etching of a flat design of the fixation device of FIGS. 3A and 3B, according to a preferred embodiment of the present invention. A mask 52 is created for etching a flat design of a fixation device. The flat design is then etched onto a piece of thin sheet metal or some other malleable material. The flat design is next cut from the sheet metal using, for example, a fine laser. The cut flat design is then polished and bent into a circular (or other) shape. Points 54 and 56 show the locations where the flat design is coupled, for example, by welding after it is bent. The welding creates an anchoring ring. Sensor support 58 is positioned approximately at the midpoint of the mask 52, but may alternatively be located at any other position. Additionally, there may be multiple sensor supports, for example, located at both sides of the fixation device design.

Figure 6:
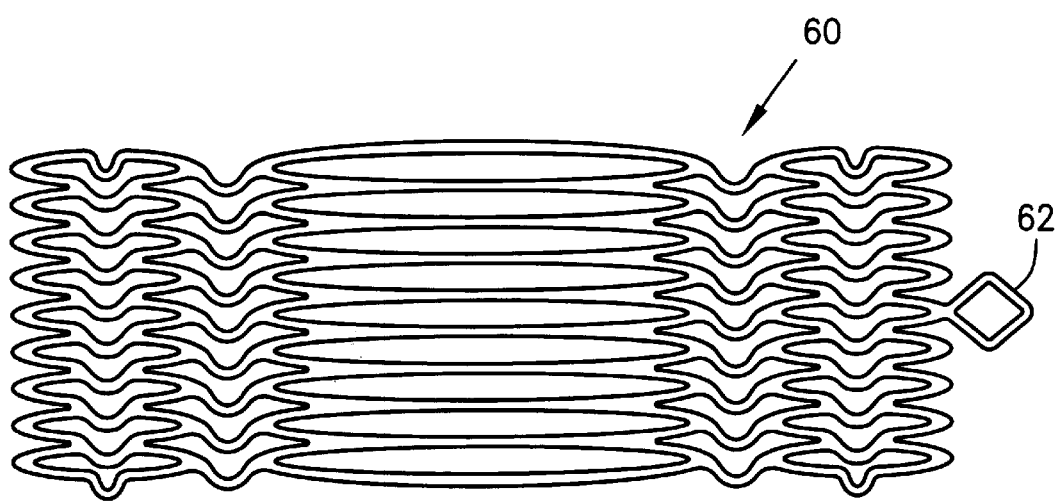
FIG. 6 shows an illustration of a mask for etching of a flat design of the fixation device of FIGS. 2A and 2B, according to a preferred embodiment of the present invention.

Referring now to FIG. 6, there is shown an illustration of a mask for etching of a flat design of the fixation device of FIGS. 2A and 2B, according to a preferred embodiment of the present invention. A mask 60 is created for etching a flat design of a stent. The flat design is then etched onto a piece of thin sheet metal or some other malleable material. The flat design is next cut from the sheet metal using, for example, a fine laser. The cut flat design is then polished and bent into a circular (or other) shape and coupled, for example, by welding after it is bent. Sensor support 62 is positioned approximately at the midpoint of the mask 60, but may alternatively be located at any other position. Additionally, there may be multiple sensor supports, for example, located at both sides of the stent design.

Figure 7:
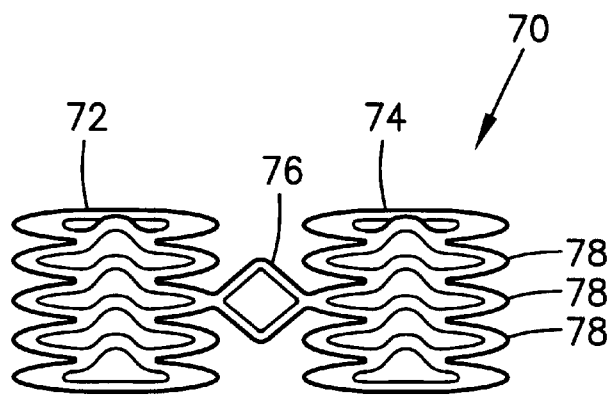
FIGS. 7 shows a fourth fixation device for a sensor before expansion, according to a preferred embodiment of the present invention.

Referring now to FIG. 7, there is shown a fourth fixation device for a sensor before expansion, according to a preferred embodiment of the present invention. A fixation device 70 in the form of a dual anchoring ring comprises a first ring 72 and a second ring 74, in a non-expanded state, with a sensor support 76 positioned between the two rings 72, 74. The fixation device 70 may be formed of any malleable material which does not revert automatically to its original shape after being expanded. The fixation device 70 is made up of a plurality of sections 78 connected one to the other to form two anchoring rings 72, 74. A sensor support 76 is connected to one of the sections 78 of each anchoring ring 72, 74 perpendicular to a cross-section of each of the rings 72, 74 forming a circular plane, and is positioned between the two rings 72, 74. The sensor support is formed in the shape of a diamond, but can be any shape desired. Additionally, there may be multiple sensor supports attached to the fixation device 70. Alternatively, the fixation device 70 may be made of two single sinusoidal rings, with one or more sensor supports attached to the peaks, since it does not serve any support function for the lumen. The fixation device 70 may alternatively be made of two stents, one on each side of a sensor support, or having multiple sensor supports attached thereto.

Figure 8:
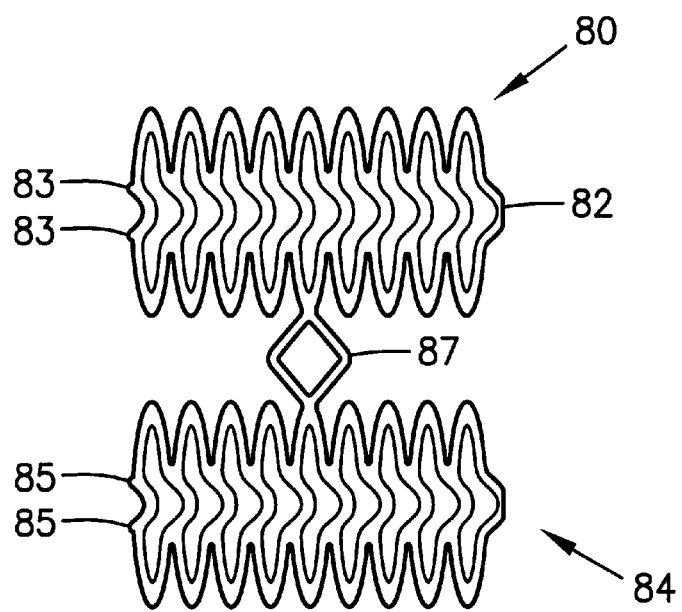
FIG. 8 shows an illustration of the fixation device of FIG. 7 in flat form, according to a preferred embodiment of the present invention.

Referring now to FIG. 8, there is shown an illustration of the fixation device of FIG. 7 in flat form, according to a preferred embodiment of the present invention. A mask 80 is created for etching a flat design of a fixation device. The flat design is then etched onto a piece of thin sheet metal or some other malleable material. The flat design is next cut from the sheet metal using, for example, a fine laser. The cut flat design is then polished and bent into a circular (or other) shape. Points 82 and 83, and points 84 and 85 show the respective locations where the flat design is coupled, for example, by welding after it is bent. The welding creates two anchoring rings. Sensor support 87 is positioned approximately at the midpoint of the mask 80, but may alternatively be located at any other position. Additionally, there may be multiple sensor supports, for example, located at both sides of the fixation device design.

Figure 9A:
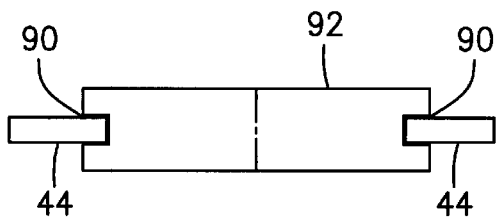
FIGS. 9A and 9B show an enlarged side view of a cross section of the sensor support from FIG. 3A along the line formed between points a' and a' according to two different embodiments of the present invention.
Figure 9B:
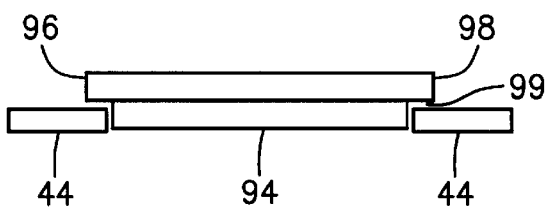

Referring now to FIGS. 9A and 9B, there is shown an enlarged side view of a cross section of the sensor support from FIG. 3A along the line formed between points a' and a'. As shown in FIG. 9A, a groove 90 is formed in two portions of the periphery of sensor 92, for example, by cutting with a wire saw, by etching, by laser cutting, etc., and the sensor 92 is then inserted into the sensor support 44 such that two portions of the sensor support 44 are positioned within the groove 90 providing support for the sensor 92. Alternatively, instead of the grooves, two notches may be formed in the periphery of the sensor 92 in which the two portions of the sensor support 44 may be positioned.

As shown in FIG. 9B, sensor 94 is formed with a lip 96 around its upper edge 98. Sensor 94 may instead be formed with one or more protrusions along its upper edge 98. Alternatively, the lip or protrusion(s) may be located on the bottom or at any other position on the sensor. The sensor 94 is coupled to the sensor support 44, for example, by glueing, welding, soldering, etc., the lip 96 or protrusion(s) to an edge or portion 99 of the sensor support. Alternatively, the sensor 94 may be placed on the sensor support 44 and supported by the lip 96 or by the protrusion(s).

Figure 10A:
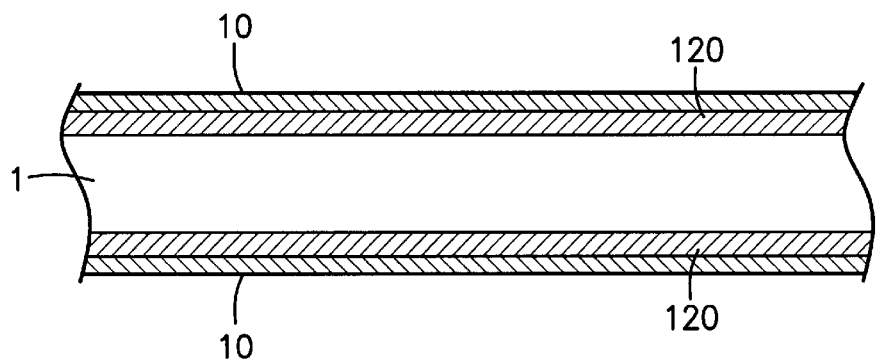
FIG. 10A shows a partial side view of a sensor that is provided with a protective layer according to the present invention.
Figure 10B:
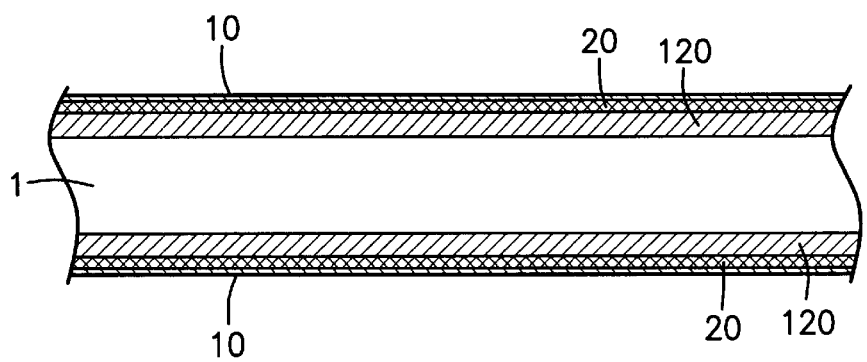
FIG. 10B shows a partial side view of a sensor that is provided with a protective layer and a surface adhesion promoter layer.

A sensor 1 that has been placed at a particular anatomical location inside a body is continuously exposed to body fluids, e.g. blood, and/or living tissue. Such body fluids and living tissue may include certain agents that degrade the membrane of sensor 1, thus rendering sensor 1 partially or totally inoperative. FIG. 10A illustrates a sensor 1 that avoids this degradation. In particular, sensor 1 (which includes membrane 120) is provided with a protective layer 10 that prevents agents present in bodily fluids and/or tissue from degrading the sensor membrane 120, which may have a thickness of 3,000 Å–5,000 Å. Sensor membrane 120 may be responsive to various external environmental influences that produce changes in its mechanical parameters, such environmental influences including pressure, flow, tissue thickness, or temperature. Underneath membrane 120, sensor may include a solid material, such as PYREX glass, or include a cavity for a medium. Although FIGS. 10A and 10B show a sensor provided with a sensor membrane 120 on either side thereof, the present invention is also applicable to sensors containing a sensor membrane 120 on only one side thereof, in which case protective layer 10 would be applied to the side provided with membrane 120. Protective layer 10 is formed of an inert, bio-compatible material that remains stable while in contact with bodily fluids and tissue throughout the entire expected operational life of sensor 1. Moreover, the material from which protective layer 10 is formed is capable of being deposited on the membrane of sensor 1 in the form of a thin layer that is uniform and flexible enough to avoid interfering with the normal operation of sensor 1. Suitable materials that may serve as protective layer 10 include, but are not limited to, silicone rubber (a commercially available example of which is MED-1511 manufactured by NuSil Technology), a fluoropolymer such as polytetrafluoroethylene (a commercially available example of which is TEFLON AF-1601 manufactured by E. I. DuPont De Nemours & Co.), and a polyxylylene polymer (an example of which is Parylene C).

Figure 10C:
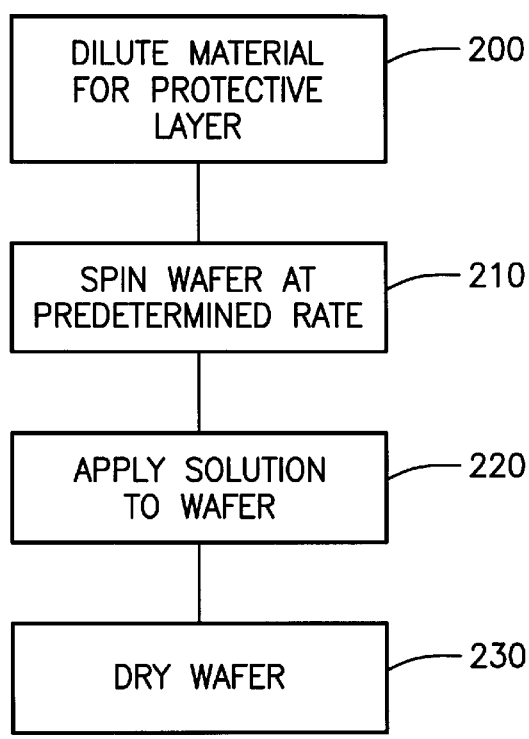
FIG. 10C illustrates a flow diagram representing a method that applies a protective layer to a wafer containing individual sensors.

FIG. 10C illustrates a flow diagram that represents an exemplary method for coating sensor 1 with a protective layer 10 composed of silicone rubber or Teflon. In this situation, the protective layer may have a thickness of about 5000 Å. The use of Parylene C as protective layer 10 will be discussed in connection with another embodiment described below. The process of FIG. 10C may be applied to wafers that are later diced in order to yield the individual sensors 1. Protective layer 10 may also be applied to the sensors 1 after the dicing operation. Returning to FIG. 10C, before the material for protective layer 10 is applied to a wafer containing the sensors 1, and in order to ensure that the protective layer 10 adheres securely to the wafer, the wafer may be pre-coated with such surface adhesion promoters as 1H, 1H, 2H, 2H, Perfluorodecyltriethoxysilane. A sensor provided with a protective layer 10 and a surface adhesion promoter layer 20 is shown in FIG. 10B. According to FIG. 10C, the material that is to serve as a protective layer 10 deposited in accordance with the steps illustrated in FIG. 10C, which may correspond to either silicone rubber or Teflon, is initially diluted to a desired degree according to any suitable dilution operation involving an appropriate solvent (step 200). The material for protective layer 10 is then applied to the wafer according to any appropriate spin coating operation during which the wafer is rotated horizontally at a rate of up to 5,000 revolutions per minute (RPM). During this spin coating operation, the wafer is rotated at the desired rate (step 210) and a solution containing the material for protective layer 10 is dripped onto a membrane-side of the spinning wafer (step 220). The rate of rotation of the wafer and the viscosity of the solution determines the thickness of the resulting protective layer 10. The protective layer 10 deposited on sensor membrane 120 may have a thickness up to 4,500 Å without significantly affecting the vibrational characteristics, and hence, accuracy, of sensor 1, although a layer 10 having a thickness less than 4,500 Å may be deposited on sensor 1 without reducing the level of protection provided by layer 10. For example, a sensor 1 provided with a layer 10 having a thickness less than 2,500 Å still would provide protection against the corrosive properties of the bodily agents and fluids to which the sensor 1 would be exposed. After the wafer has been coated with the material of the protective layer 10, the wafer undergoes a drying operation (step 230). The process for depositing layer 10 may be applied for each side of the wafer that is to have layer 10 deposited thereon. If the material for the protective layer 10 is silicone rubber, then the coated wafer is air dried, at which point any solvent residue is removed and acetic acid is emitted; if the material for the protective layer 10 is Teflon, then the coated wafer undergoes a thermal cycle that cures the wafer and includes a low temperature cycle during which any solvent residue is removed followed by a higher temperature cycle.

After the wafer has dried, the wafer is diced in order to yield the individual sensors 1. If protective layer 10 includes Teflon, the Teflon may first be removed from the path of the dicing saw so that the Teflon protective layer 10 is not damaged during the dicing operation. The Teflon may be removed from the path of the dicing saw through any appropriate method. For example, the Teflon may be removed from the dicing path by a plasma etching operation that is performed through a photoresist mask that exposes only the dicing path pattern. Furthermore, the above-described process may be applied to both sides of the wafer in order to produce sensors 1 having the protective layer 10 applied to multiple sides thereof.

Figure 11:
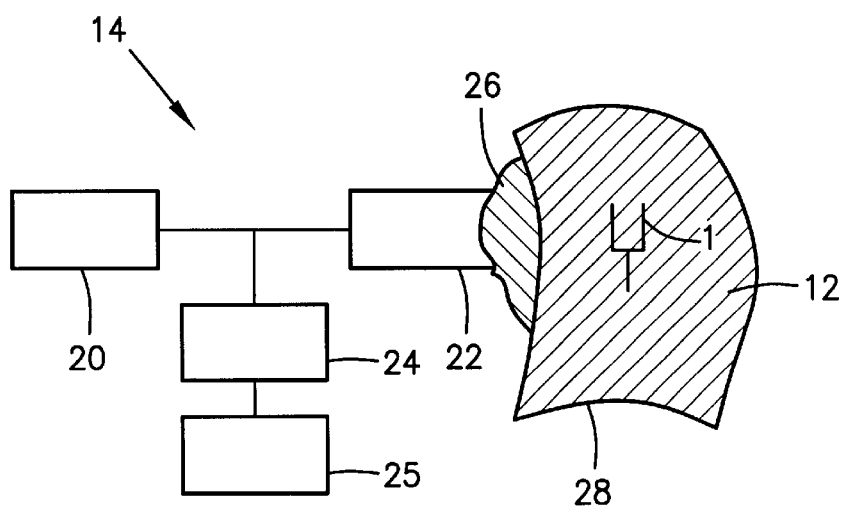
FIG. 11 illustrates an ultrasonic passive sensor system that includes a passive sensor to which the protective layer of the present invention may be applied.

FIGS. 11–14 illustrate examples of sensors that may serve as sensor 1, and to which the protective layer discussed above (and to be discussed below) may be applied. These exemplary illustrations of the kinds of sensors that may serve as sensor 1 are described in U.S. Pat. No. 5,619,997. Reference is now made to FIG. 11 which illustrates an ultrasonic sensor system. The system comprises a passive sensor 1 and an external ultrasonic activation and detection system 14. The sensor 1 is implantable in an ultrasound compatible medium 12, such as the human body, or mountable on an inner wall of an enclosure.

The sensor 1 is any suitable sensor, examples of which are described herein below with respect to FIGS. 12–14, which mechanically vibrates in the presence of an ultrasonic wave, much as a tuning fork vibrates in the presence of a sonic wave. Therefore, sensor 1 is represented schematically in FIG. 11 as a tuning fork. The frequency of vibration of sensor 1 is at its current vibration frequency which is a function at least of the physical variable being sensed.

The activation and detection system 14 typically includes an ultrasonic generator 20, at least one ultrasonic transducer 22, a frequency detector 24, and a data processor 25. The ultrasonic generator 20 and transducer 22 constitute the activating elements and the transducer 22, the frequency detector 24, and the data processor 25 constitute the detecting elements.

The generator 20, such as the non destructive testing unit, model IIB USDF, manufactured by Balteu Sonatest/ Schlumberger of Milton Keynes, England, generates an ultrasonic wave to be transmitted by the ultrasonic transducer 22 to the sensor 1 via the medium 12. Typically, ultrasonic gel 26, located on an outer edge 28 of medium 12, is utilized to couple the transducer 22 to the medium 12. Typically, the transmitted ultrasonic wave is composed of a single frequency or a range of frequencies. For example, any suitable chirping transmission operation may be implemented with respect to the ultrasonic wave generating system described above, in which multiple ultrasonic tone bursts, perhaps 20 microseconds apart and each corresponding to a different frequency, are successively transmitted to the sensor 1. Thus, this operation corresponds to a frequency scan operation in which the sensor 1 is exposed to a plurality of ultrasonic tone bursts separated in time and corresponding to a different frequency. As an alternative to this chirping operation, the ultrasonic wave generating system described above may instead be configured according to any suitable transmission scheme for transmitting a single pulse embodying an ultrasonic signal containing a plurality of frequencies that impinge on sensor 1. The frequency domain representation of such a pulse would resemble that of a Gaussian distribution. For both of these ultrasonic wave generation techniques, the frequencies of the transmitted ultrasonic waves may have a value ranging from 500 kHz to 1 MHZ.

The ultrasonic transducer 22, such as one part of the non-destructive testing unit, typically also receives ultrasonic waves from the medium 12. Some of these waves are reflections of the transmitted wave; others are from sensor 1. In an alternative embodiment, there are two ultrasonic transducers 22, one for transmitting and one for receiving.

If the transmitted ultrasonic waves include a frequency at the current resonant frequency of the sensor 1, the sensor 1 will vibrate at this resonant frequency. Because the sensor 1 absorbs the energy of the ultrasonic waves at the resonant frequency, the reflected waves received by transducer 22 have an amplitude at the resonant frequency that is less than the amplitude of the reflected waves at the other frequencies. In addition, the sensor 1 continues to vibrate even after transmission of ultrasonic waves has stopped.

The frequency detector 24, similar to the 8590A spectrum analyzer manufactured by Hewlett Packard Inc. of the U.S.A., analyzes the received ultrasonic waves to determine which frequency has been absorbed by sensor 1 and/or at which frequency the sensor 1 resonates when no longer excited by the transmitted ultrasonic waves.

Data processor 25 converts the frequency determined by the frequency detector 24 into the value of the physical variable being measured. The information needed for this conversion depends on the actual structure of the sensor 1, as described in more detail hereinbelow.

It will be appreciated that the system of FIG. 11 is implantable deep within living tissue or within a conductive enclosure. As explained above, the system operates with mechanical vibration rather than electromagnetic resonance.

Figure 12A:
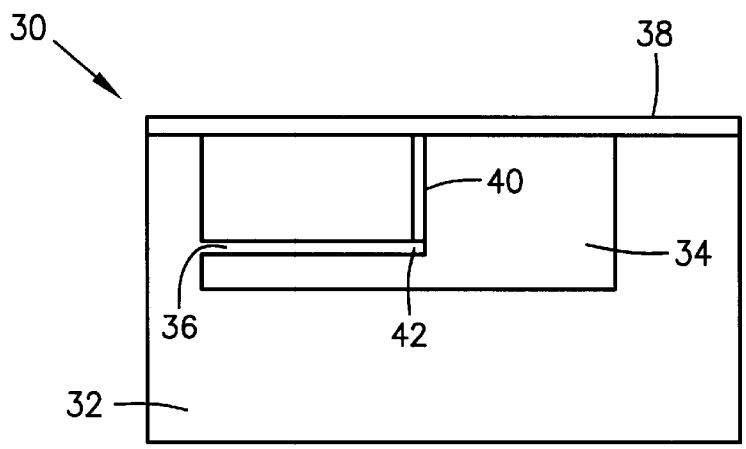
FIG. 12A is a schematic illustration of a passive sensor useful in the system of FIG. 11.
Figure 12B:
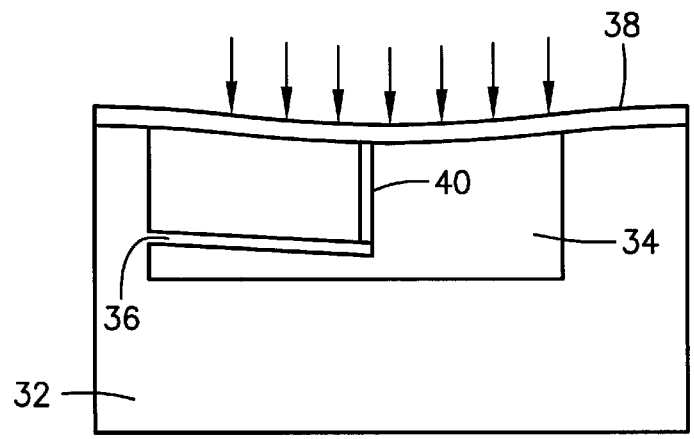
FIG. 12B is a schematic illustration of the sensor of FIG. 12A in the presence of pressure.

Reference is now made to FIGS. 12A and 12B, which illustrate an exemplary passive sensor that may serve as sensor 1. The sensor of FIGS. 12A and 12B, labeled 30, is responsive to pressure. FIGS. 12A and 12B illustrate the sensor 30 in the absence and presence, respectively, of pressure.

Sensor 30 is typically machined from silicon and typically comprises a cup-shaped housing 32 having a recess 34, a vibratable beam 36, a membrane 38, and a coupler 40. The material from which sensor 30 is machined, including membrane 38, may also include silicon nitride or silicon dioxide.

The vibratable beam 36 is typically integrally attached to the housing 32 and extends into recess 34. The coupler 40 typically connects between membrane 38 and a far end 42 of beam 36. The coupler 40 is either integrally attached to the membrane 38 or the vibratable beam 36. Sensor 30 may be machined to have a cross-sectional thickness of 100 $\mu$m, and each side may be machined to have a length of 400 $\mu$m. Moreover, membrane 38 may have a thickness in the range of 0.3 to 0.5 $\mu$m. Sensor 30 may be configured according to dimensions other than those given above without departing from the scope of the present invention. Moreover, these dimensions may characterize the size of any of the other sensors described herein.

As shown in FIG. 12B, membrane 38 typically bends into recess 34 in response to pressure from the outside. This causes coupler 40, which is stiff, to press on far end 42, inducing beam 36 to bend and thus, straining it. As is known in the art, a strained beam vibrates at a higher frequency than a non-strained beam. Thus, the higher the pressure on membrane 38, the higher the vibration frequency of beam 36. Moreover, when beam 36 vibrates, the membrane 38 vibrates as well. The specific relationship between pressure and frequency of beam 36 depends on the material of beam 36, its length and its cross-sectional area and to some extent on other factors, such as temperature and viscosity of whatever medium is within recess 34.

It is noted that, if the membrane 38 was made of many materials or coated with other materials, it would bend in response to other physical variable, such as temperature. For example, FIG. 12C illustrates a sensor responsive to temperature and FIG. 14B, described hereinbelow, illustrates a sensor responsive to chemical composition.

Figure 12C:
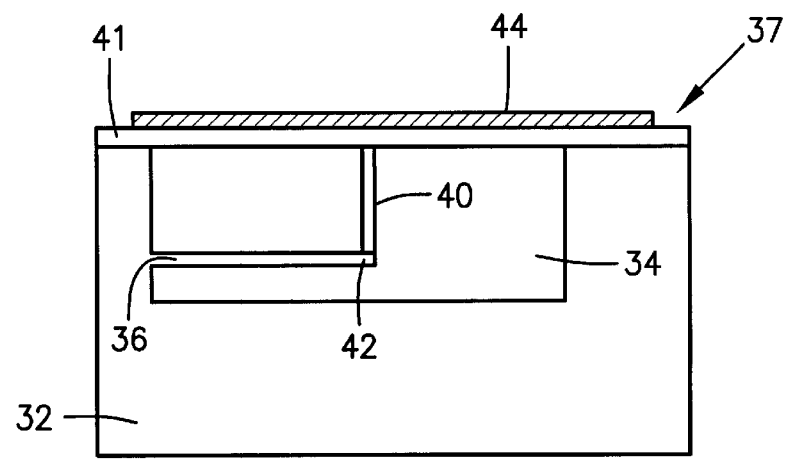
FIG. 12C is a schematic illustration of a passive sensor which is sensitive to temperature.

Reference is now briefly made to FIG. 12C. In this sensor, the membrane 37 is made of two materials, 41 and 44, each having different thermal coefficients. Exemplary materials are silicon and silicon nitride. Since the materials expand and contract at different rates, the membrane 37 will buckle as a function of the temperature.

Figure 13A:
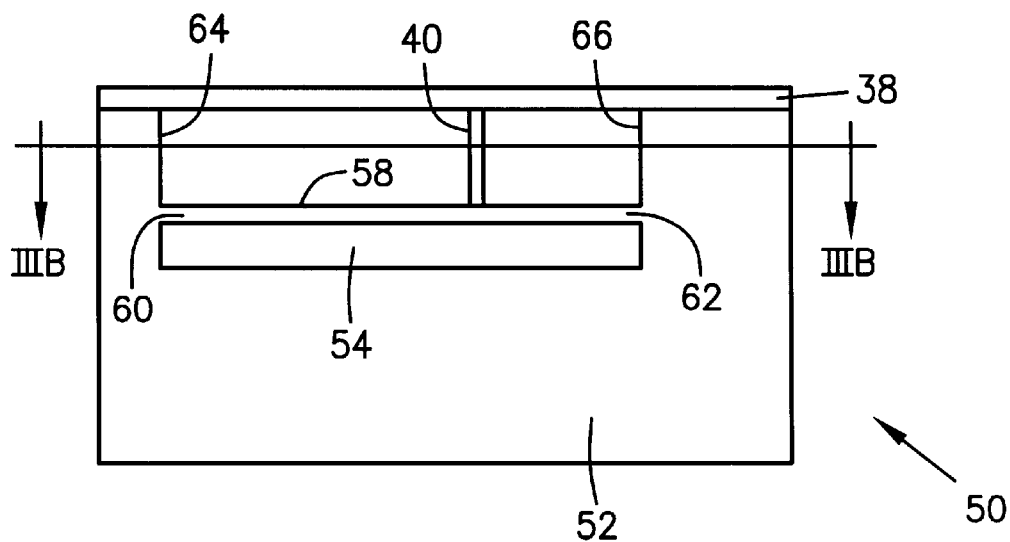
FIG. 13A is a side view of an alternative passive sensor having two coupled vibrating beams and a reference beam.
Figure 13B:
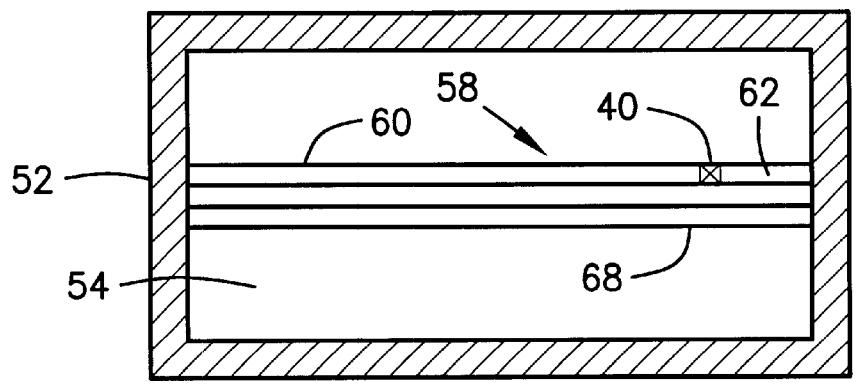
FIG. 13B is a top view of the sensor of FIG. 13A.

Reference is now made to FIGS. 13A and 13B, which illustrate an alternative embodiment of the passive sensor which has different transmission and reception frequencies. Furthermore, the sensor of FIGS. 13A and 13B also has a reference frequency. FIG. 13A is a side view of the sensor, labeled 50, and FIG. 13B is a top view taken along lines IIIB—IIIB of FIG. 13A.

The sensor 50 is similar to sensor 30 in that it has a housing, labeled 52, and a recess 54. However, the vibratable element of sensor 50 is a full length beam 58. Similar to sensor 30, sensor 50 also has a membrane 38 and a coupler 40. In this embodiment, coupler 40 is connected to beam 58 somewhere other than at its middle so as to create two separate but coupled vibratable beams 60 and 62 which vibrate at different frequencies.

As illustrated in FIG. 13A, beam 60, defined as the length of beam 58 from a left edge 64 of housing 52 to coupler 40, is longer than beam 62, defined as the length of beam 58 from a right edge 66 of housing 52 to coupler 40. Therefore, beam 60 vibrates at a lower frequency than beam 62.

In the presence of pressure, membrane 38 bends, pushing coupler 40 further into recess 54 and bending beam 58, straining both beams 60 and 62. When in operation, the sensor system excites sensor 50 with an ultrasonic wave whose range of frequencies is approximately the range of vibration frequencies of long beam 60. The long beam 60 becomes excited and its excitation causes short beam 62 also to vibrate, but at its current vibration frequency. In response to the vibration of beams 60, 62, membrane 38 vibrates as well.

Since the short beam 62 typically has a vibration frequency range significantly different than that of the long beam 60, the ultrasonic transducer 22 and frequency detector 24 need only be tuned, for reception purposes, to the frequency range of short beam 62. Since only the short beam 62 will be active in its frequency range, the signal to noise (S/N) ratio of the signal received by the transducer 22 will be high since there will be little or not noise associated with the excitation frequency.

The sensor 50 can optionally also include a reference beam 68 (FIG. 13B), located next to beam 58. Beam 68 is connected at both ends to housing 52 but is not connected at both ends to coupler 40. Therefore, the vibration frequency of beam 68 does not change with pressure. Any changes of its vibration frequency must therefore be due to other causes, such as temperature, viscous damping, etc., which also affect the beams 60 and 62. The output of reference beam 68 is thus utilized, by data processor 25, to correct the pressure values determined from beams 60 and 62.

Figure 14A:
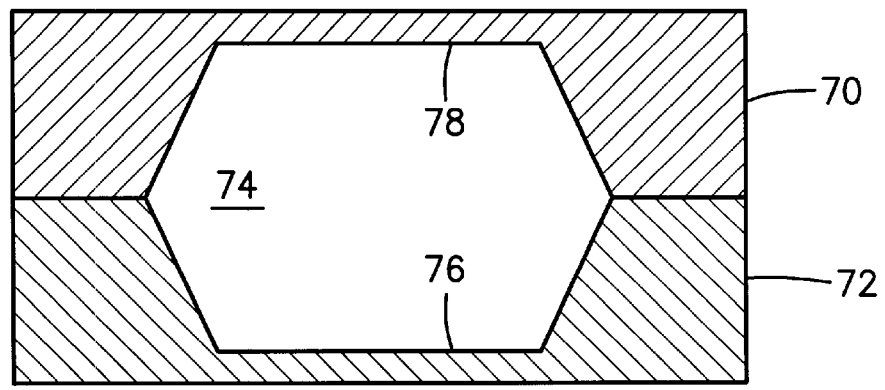
FIG. 14A is a schematic illustration of an alternative two membrane passive sensor.

Reference is now briefly made to FIG. 14A, which illustrates a further alternative embodiment of the sensor formed of two silicon wafers 70 and 72. Typically, each wafer is formed into roughly a squared off cup shape and the two are bonded together so as to produce an enclosed space 74. The base of each cup is flat, forming a membrane which can freely vibrate into space 74. In order to provide the sensor of FIG. 14A with two different, coupled frequencies, the thickness of the membranes, labeled 76 and 78, is different.

As in the embodiment of FIG. 13A, the vibrating element with the lower vibration frequency, (i.e. thin membrane 78) receives the ultrasonic signal and the other membrane, thick membrane 76, transmit the reflected ultrasonic signal. The two vibrating elements are coupled via the sides of the wafers 70 and 72 and through whatever medium is placed into enclosed space 74.

Figure 14B:
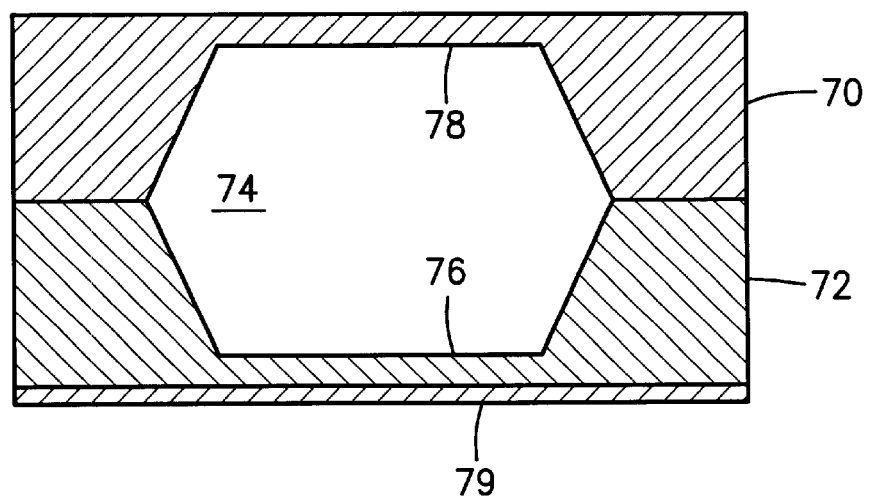
FIG. 14B is a schematic illustration of a passive sensor that is sensitive to chemical compositions.

A sensor similar to that shown in FIG. 14A can be used to measure chemical composition. The resultant sensor is illustrated in FIG. 14B to which reference is now made. The thick membrane 76 of FIG. 14B is coated with a thin, soft, polymeric film 79 which absorbs gas phase analytes. The analytes add weight to film 79 and change its viscoelasticity. As a result, the vibration frequency changes.

Contrary to the prevalent view, it was discovered that a sensor 30 machined from silicon, including one in which membrane 38 is formed from a single crystalline silicon, does not exhibit a satisfactory degree of bio-compatibility with the naturally occurring bodily fluids and agents it encounters when implanted inside a patient. Indeed, when the membrane 38 of such a sensor 30 is exposed for a long enough time to such an environment, such as three months, the membrane 38 may dissolve completely, rendering sensor 30 useless. This vulnerability applies to the other types of sensors discussed above as well. In order to explain the manner in which this vulnerability is minimized through the use of a protective coating, reference shall be made to the pressure sensitive sensor 30 of FIGS. 12A–12C, with the understanding that the steps taken to protect the sensor 30 of FIGS. 12A–12C apply as well to the other types of sensors discussed above.

As explained above, sensor 30 includes a membrane 38 that is mechanically deformed by a certain deflection in response to the application of a pressure thereon. As membrane 38 changes shape according to such a deflection, so too does the resonant frequency of membrane 38 change. Once an ultrasonic wave with a frequency matching that of the membrane resonant frequency is exposed to membrane 38, membrane 38, along with beam 36, absorbs the energy of the ultrasonic wave at that frequency and begins to vibrate mechanically at that resonant frequency, generating a reflection wave that is picked up at the system of FIG. 11. Stated another way, when an ultrasonic wave, which may have its particular frequency domain characteristic represented as a Fourier transform, is transmitted to the sensor 30, the membrane 38 will absorb the wave energy occurring at the particular resonant frequency of the membrane, which depends on the amount by which the membrane 38 is deflected because of such external influences such as pressure. Because the energy absorption by membrane 38 will occur at the resonant frequency of membrane 38, the Fourier transform representation of the reflected wave produced by membrane 38 will exhibit a particular notch (a sharp decrease in amplitude) at this frequency. This notch is at the frequency at which the membrane 38 absorbs the energy of the transmitted ultrasonic wave. Therefore, this notch frequency is considered to be the resonant frequency of membrane 38. This frequency may be detected by any suitable analysis device, or the frequency may be determined visually by inspecting an image of the Fourier transform provided to any suitable display. Since the resonant frequency of membrane is proportional to the pressure acting on membrane, the pressure acting on the membrane 38 can be derived from the measured resonant frequency.

As explained above, if membrane 38 is exposed for a long enough time to the naturally occurring fluids and agents occurring inside a body, the silicon out of which membrane 38 is formed will begin to erode; this erosion will affect the vibrational characteristic of membrane 38. As the membrane 38 continues to erode, the accuracy of the measurement provided by such a resonant frequency determination as discussed above is consequently degraded. In order to prevent this degradation, a protective coating is applied to membrane 38.

Figure 15:
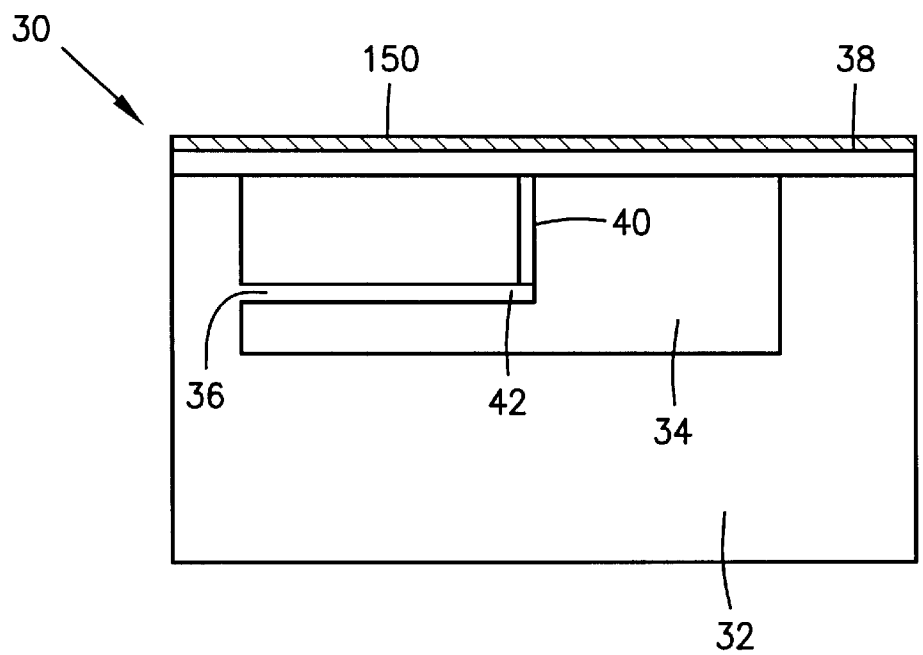
FIG. 15 is a schematic illustration of a passive sensor provided with a protective layer formed from a polyxylylene polymer material.

FIG. 15 illustrates a sensor 30 in which an exemplary protective layer 150 of a polyxylylene polymer material is deposited on membrane 38. Of course, the material for the protective layer 150 in FIG. 15 need not be limited to a polyxylylene polymer, but instead may be formed from silicone rubber or polytetrafluoroethylene in the manner discussed above. When a polyxylylene polymer is used as the material for protective layer 150, one example of polyxylylene that may be applied to sensor 30 is Parylene C (poly(p-chloroxylylene). Other polyxylylene polymers that may be applied to sensor 30 include, but are not limited to, Parylene N (poly(p-xylylene)), Parylene D (poly(p-dichloroxylylene)), and Parylene VIP™ AF-4 (poly(p-tetrafluoroxylylene)). Thus, although the following discussion focuses on Parylene C as the material for protective layer 150, it will be appreciated that any of the polyxylylene materials mentioned above may serve as protective layer 150. Further, although the exemplary sensor 30 to which the Parylene C protective layer 150 is applied is the sensor shown in FIG. 12A, the Parylene C protective layer may be applied not only to this sensor 30, but to any of the sensors described herein. Moreover, with respect to the particular embodiment illustrated in FIG. 15, sensor 30 may be configured according to the 400 μm×400 μm×100 μm dimensions mentioned in connection with FIG. 12A, and the thickness of membrane 38 may also correspond to the thickness of 0.3 μm–0.5 μm discussed above in connection with FIG. 12A. Finally, although FIG. 15 illustrates protective layer 150 as being deposited on only one side of sensor 30, protective layer 150 may be deposited on as many sides of sensor 30 as is desired.

In FIG. 15, protective layer 150 has a thickness not more than about 4,500 Å for a sensor 30. Protective layer 150 provides enough resistance to bodily fluids and other degrading agents in the patient's body that the structural and functional integrity of membrane 38 is preserved without significant degradation. This protective function is also provided by a layer 150 that is thinner than 4,500 Å. In fact, a layer 150 having a thickness less than about 2,500 Å may be applied to membrane 38 without reducing the protection provided by layer 150. Because the thickness of protective layer 150 is smaller than that of membrane 38, the sensitivity of membrane 38 with protective layer 150 remains about the same as that of a membrane 38 provided with no protective layer 150. On the other hand, as the thickness of protective layer 150 is increased to dimensions beyond about 4,500 Å, interference with the sensitivity of membrane 38 becomes significant enough to affect the accuracy of the data obtained from sensor 30. In particular, as the coating thickness becomes greater than 4,500 Å, the amplitude (or Q factor) of the resonance is diminished, which renders the readings provided by sensor 30 less accurate. This is in contrast with previously proposed active sensors that employ a deflectable membrane. In such active sensors, the membrane deflects in response to an external condition, but does not vibrate at a resonant frequency in response to an ultrasonic wave. Thus, unlike the membrane 38 of sensor 30, which is capable of being deflected and of vibrating at a predetermined resonant frequency, the membrane of such a previously proposed sensor remains stationary at its deflected configuration. Instead of providing data regarding the measured bodily characteristic via an ultrasonic reflection wave, such an active sensor produces an electrical signal that is proportional to the amount by which the membrane is deflected. Because the membrane of such previously proposed active sensors do not resonate, they may employ protective coatings of much greater thickness than 4,500 Å.

Figure 16:
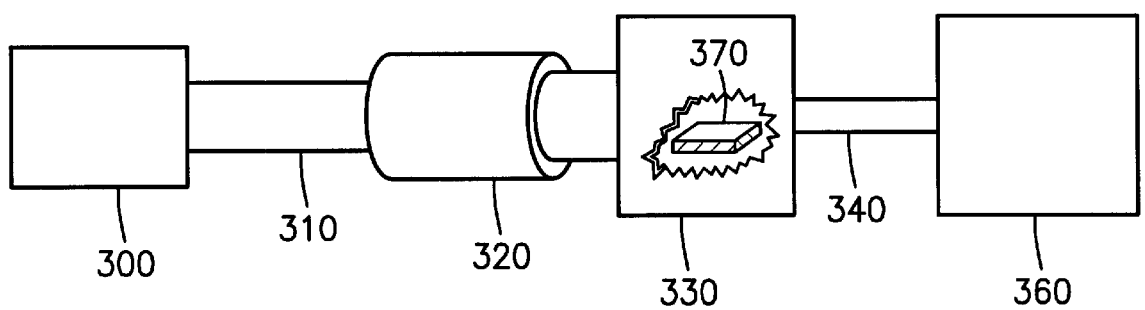
FIG. 16 is a schematic illustration of a vapor deposition arrangement for depositing the protective layer shown in FIG. 15 onto the passive sensor.

Returning to FIG. 15, protective layer 150 is deposited on sensor 30 according to any suitable vapor deposition technique compatible with the deposition of a polyxylylene polymer material. For example, as shown in FIG. 16, a vapor deposition arrangement includes a vaporization chamber 300, a pyrolysis (reaction) chamber 320 connected to vaporization chamber 300 via tube 310, a deposition chamber 330 coupled to pyrolysis chamber 320 and including a condensation stage 370, and a vacuum pump 360 coupled to deposition chamber 330 via tube 340. Vaporization chamber 300 vaporizes a dimer of polyxylylene polymer material (di-p-xylylene) at a temperature of about 150° C. and pressure of about 1 Torr. The dimer is then pyrolyzed at about 680° C. and 0.5 Torr to produce a monomer such as p-xylylene. The monomer then enters the deposition chamber 330 at an ambient temperature (room temperature), where the sensor 30, either individually or as part of a wafer containing many sensors 30, is located. At this point, the monomer is absorbed and polymerized onto sensor 30 to produce protective layer 150. If the sensor 30 is placed in deposition chamber 330 individually, then protective layer 150 would be applied to all exposed surfaces of the sensor 30. On the other hand, if sensor 30 is placed in deposition chamber 330 as part of a wafer containing many sensors 30, then the polyxylylene polymer material will be deposited on sensor 30 in the manner shown in FIG. 15. In that situation, after the wafer is diced to produce the individual sensors 30, the sides of such sensors will not be coated with the polyxylylene polymer material because those surfaces were not exposed during the deposition process. In that situation, only membrane 38 of sensor 30, as shown in FIG. 15, will be coated with the protective layer 150 of polyxylylene polymer material.

In order to be able to deposit a protective layer 150 on sensor 30 that is less than 4,500 Å, the above-described vapor deposition process is carried out more slowly than previously proposed vapor deposition processes. For instance, while some previously proposed vapor deposition processes take only about 10 seconds to deposit polyxylylene polymer material on a surface, the protective layer 150 according to the present invention may be deposited according to a vapor deposition process that takes as long as ten minutes. By performing the deposition process at this rate, the vapor deposition process for depositing protective layer 150 on sensor 30 may be controlled more precisely to achieve the desired protective layer thickness and prevent the formation of pin-holes. Any suitable deposition monitor (not shown) may be coupled to the deposition chamber 330 to allow a person operating the deposition chamber to keep track of the protective layer material as it accumulates on sensor 30 during the deposition process. Once the thickness of the protective layer 150 achieves the desired value, the person monitoring the deposition can shut off the process, or such a process may be terminated automatically upon the monitored thickness achieving the desired value. Moreover, since different areas of deposition chamber 330 exhibits different rates of deposition, in order to ensure that the material for protective layer 150 is deposited on sensor 30 at the desired rate, the sensor 30 may be placed in that area of deposition chamber 330 that exhibits a slower rate of deposition than other areas.

With protective layer 150 deposited on membrane 38, sensor 30 becomes more resistant to the corrosive characteristics of the bodily fluids encountered when sensor 30 is implanted inside a patient. Because of this protective layer 150, sensor 30 remains intact inside a patient, and, consequently, produces accurate data for a period of time that is greater than if sensor 30 included no such protective layer 150.

In addition to the permanent layer as described above, or as an alternative where suitable, a temporary coating may be placed on the sensors to protect them from damage and/or destruction during deployment. The temporary coating may be made from a material that is soluble in an aqueous solution, and should dissolve immediately or soon after deployment of the sensor. The material used, the thickness of the temporary coating and the hardness of the temporary coating will depend to a large extent on the location of the sensor, the type of sensor, and a variety of other factors including the physiology involved, the parameters being measured, and the desired speed of deployment.

A first example of a temporary coating is a composition comprising solidified sugar syrup made of approximately equal amounts of glucose and sucrose. The proportions of glucose and sucrose may be varied, however, depending on the application.

A second example of a temporary coating is a composition comprising Hydroxy Propyl Methyl Cellulose, Hydroxy Propyl Cellulose and Colloidal Silicone Dioxide, all finely ground and mixed in water, which is used for coating pills and is commercially available as Opadry-Oy-34817 from Colorcon Ltd., Italy.

Other materials may be used as a temporary protective coating for a sensor. The temporary protective coating may be made from any other substance which is hard or thick enough to protect the sensor from damage during insertion, dissolves immediately or soon after insertion and is biocompatible in the intended location of deployment in the body.

A sensor may be coated by any available method for coating objects including, for example, spraying the coating on the sensor, dipping the sensor in a liquid bath, pouring or dripping the coating onto the sensor, painting the coating onto the sensor, etc. Additionally, the coating may cover only the membrane of the sensor or it may cover a larger portion of the sensor or the entire sensor.

What is claimed is:

1. A device for implantation into an anatomical location inside a body, comprising:

a sensor including a mechanically vibratable membrane; and a protective layer formed from a polyxylylene polymer material and deposited on at least the mechanically vibratable membrane.

2. The device according to claim 1, wherein the protective layer has a thickness less than 4,500 Å.

3. The device according to claim 1, wherein the protective layer has a thickness that is less than 2,500 Å.

4. The device according to claim 1, wherein the mechanically vibratable membrane is formed from a semiconductor material.

5. The device according to claim 4, wherein the semiconductor material includes one of silicon, silicon nitride, and silicon dioxide.

6. The device according to claim 1, wherein the mechanically vibratable membrane is responsive to an anatomical characteristic of the body.

7. The device according to claim 1, wherein the protective layer prevents body fluids and tissue from degrading an operation of the mechanically vibratable membrane.

8. The device according to claim 1, wherein the protective layer includes an inert material.

9. The device according to claim 1, wherein the protective layer includes a bio-compatible material.

10. The device according to claim 1, wherein the polyxylylene polymer material includes one of poly(p-chloroxylylene), poly(p-xylylene), poly(p-dichloroxylylene), and poly(p-tetrafluoroxylylene).

11. The device according to claim 1, wherein the sensor is a passive sensor.

12. The device according to claim 6, wherein the anatomical characteristic to which the mechanically vibratable membrane is responsive includes at least one of a pressure, a temperature, and a chemical.

13. A device for implantation at an anatomical location inside a body, comprising:

a sensor having a mechanically vibratable membrane; and a protective layer formed from a silicone rubber material and deposited on at least the mechanically vibratable membrane.

14. The device according to claim 13, wherein the protective layer has a thickness less than 5000 Å.

15. A device for implantation at an anatomical location inside a body, comprising:

a sensor having a mechanically vibratable membrane; and a protective layer formed from a polytetrafluoroethylene material and deposited on at least the mechanically vibratable membrane.

16. The device according to claim 15, wherein the protective layer has a thickness less than 5000 Å.

17. The device according to claim 16, further comprising an adhesion promoter layer applied between at least one surface of the sensor and the protective layer.

18. The device according to claim 17, wherein the adhesion promoter layer includes perfluorodecyltriethoxysilane.

* * * * *